United States Patent
Su

(10) Patent No.: US 11,492,387 B2
(45) Date of Patent: Nov. 8, 2022

(54) BROAD SPECTRUM VACCINE, PREPARING METHOD AND APPLICATION THEREOF

(71) Applicant: Tianjin Dongya Biological Technology Co., Ltd., Tianjin (CN)

(72) Inventor: Dianjie Su, Tianjin (CN)

(73) Assignee: Tianjin Dongya Biological Technology Co., Ltd., Tianjing (CN)

( * ) Notice: Subject to any disclaimer, the term of this patent is extended or adjusted under 35 U.S.C. 154(b) by 203 days.

(21) Appl. No.: 15/975,754

(22) Filed: May 9, 2018

(65) Prior Publication Data
US 2019/0345221 A1 Nov. 14, 2019

(51) Int. Cl.
*C07K 14/74* (2006.01)
*A61K 39/145* (2006.01)
*A61K 39/00* (2006.01)

(52) U.S. Cl.
CPC . *C07K 14/70539* (2013.01); *A61K 39/001111* (2018.08); *A61K 39/145* (2013.01)

(58) Field of Classification Search
None
See application file for complete search history.

(56) References Cited

U.S. PATENT DOCUMENTS

| 2012/0177671 A1* | 7/2012 | Rulleau | A61K 39/001 424/185.1 |
| 2015/0110802 A1* | 4/2015 | Chowdhury | C07K 16/2803 424/145.1 |
| 2016/0272724 A1* | 9/2016 | Loustau | A61K 39/0005 |

FOREIGN PATENT DOCUMENTS

WO  WO-9631604 A1 * 10/1996  ....... C07K 14/70539

OTHER PUBLICATIONS

Geraghty (PNAS USA Dec. 1987 84: 9145-9149) (Year: 1987).*

* cited by examiner

*Primary Examiner* — Peter J Reddig
(74) *Attorney, Agent, or Firm* — Helen S Liu

(57) ABSTRACT

The use of an HLA-G molecule and its antigenic fragments prepared a broad spectrum vaccine which could be used to prevent the invasion of various tumors and various viruses or unknown virus on human and animal body.

6 Claims, No Drawings
Specification includes a Sequence Listing.

SEQUENCE LISTING

```
<160> NUMBER OF SEQ ID NOS: 12

<210> SEQ ID NO 1
<211> LENGTH: 13
<212> TYPE: PRT
<213> ORGANISM: Artificial Sequence
<220> FEATURE:
<223> OTHER INFORMATION: The genetic source is human.

<400> SEQUENCE: 1

Tyr Trp Glu Glu Glu Thr Arg Asn Thr Lys Ala His Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: The genetic source is human.

<400> SEQUENCE: 2

Arg Gly Tyr Tyr Asn Gln Ser Glu Ala Ser Ser His Thr Leu
1               5                   10

<210> SEQ ID NO 3
<211> LENGTH: 13
<212> TYPE: PRT
<213> ORGANISM: Artificial Sequence
<220> FEATURE:
<223> OTHER INFORMATION: The genetic source is human.

<400> SEQUENCE: 3

Pro Pro Lys Thr His Val Thr His His Pro Val Phe Asp
1               5                   10

<210> SEQ ID NO 4
<211> LENGTH: 11
```

```
<212> TYPE: PRT
<213> ORGANISM: Artificial Sequence
<220> FEATURE:
<223> OTHER INFORMATION: The genetic source is human.

<400> SEQUENCE: 4

Pro Leu Met Leu Arg Trp Lys Gln Ser Ser Leu
1               5                   10

<210> SEQ ID NO 5
<211> LENGTH: 338
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (83)..(95)
<223> OTHER INFORMATION: SEQ ID NO: 1 SEQUENCE
<220> FEATURE:
<221> NAME/KEY: MISC_FEATURE
<222> LOCATION: (106)..(119)
<223> OTHER INFORMATION: SEQ ID NO: 2 SEQUENCE
<220> FEATURE:
<221> NAME/KEY: MISC_FEATURE
<222> LOCATION: (208)..(220)
<223> OTHER INFORMATION: SEQ ID NO: 3 SEQUENCE
<220> FEATURE:
<221> NAME/KEY: MISC_FEATURE
<222> LOCATION: (293)..(303)
<223> OTHER INFORMATION: SEQ ID NO: 4 SEQUENCE

<400> SEQUENCE: 5

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
```

```
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
                260                 265                 270

Val Pro Ser Gly Glu Glu Gln Arg Tyr Thr Cys His Val Gln His Glu
                275                 280                 285

Gly Leu Pro Glu Pro Leu Met Leu Arg Trp Lys Gln Ser Ser Leu Pro
            290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp

<210> SEQ ID NO 6
<211> LENGTH: 246
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (83)..(95)
<223> OTHER INFORMATION: SEQ ID NO: 1 sequence
<220> FEATURE:
<221> NAME/KEY: MISC_FEATURE
<222> LOCATION: (116)..(128)
<223> OTHER INFORMATION: SEQ ID NO: 3 sequence
<220> FEATURE:
<221> NAME/KEY: MISC_FEATURE
<222> LOCATION: (201)..(211)
<223> OTHER INFORMATION: SEQ ID NO: 4 sequence

<400> SEQUENCE: 6

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
                20                  25                  30

Ser Ala Ala Val Ser Arg Pro Gly Arg Gly Glu Pro Arg Phe Ile Ala
            35                  40                  45

Met Gly Tyr Val Asp Asp Thr Gln Phe Val Arg Phe Asp Ser Asp Ser
        50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Asp Pro Pro Lys Thr His Val Thr His His Pro Val Phe Asp
        115                 120                 125

Tyr Glu Ala Thr Leu Arg Cys Trp Ala Leu Gly Phe Tyr Pro Ala Glu
    130                 135                 140

Ile Ile Leu Thr Trp Gln Arg Asp Gly Glu Asp Gln Thr Gln Asp Val
145                 150                 155                 160

Glu Leu Val Glu Thr Arg Pro Ala Gly Asp Gly Thr Phe Gln Lys Trp
                165                 170                 175

Ala Ala Val Val Val Pro Ser Gly Glu Glu Gln Arg Trp Thr Cys His
            180                 185                 190
```

```
Val Gln His Glu Gly Leu Pro Glu Pro Leu Met Leu Arg Trp Lys Gln
        195                 200                 205

Ser Ser Leu Pro Thr Ile Pro Ile Met Gly Ile Val Ala Gly Leu Val
        210                 215                 220

Val Leu Ala Ala Val Val Thr Gly Ala Ala Val Ala Ala Val Leu Trp
225                 230                 235                 240

Arg Lys Lys Ser Ser Asp
                245

<210> SEQ ID NO 7
<211> LENGTH: 143
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (83)..(95)
<223> OTHER INFORMATION: SEQ ID NO: 1 sequence

<400> SEQUENCE: 7

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Gln Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Gly Ile Val Ala Gly Leu Val Val Leu Ala Ala Val Val Thr
        115                 120                 125

Gly Ala Ala Val Ala Ala Val Leu Trp Arg Lys Lys Ser Ser Asp
    130                 135                 140

<210> SEQ ID NO 8
<211> LENGTH: 235
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (83)..(95)
<223> OTHER INFORMATION: SEQ ID NO: 1 sequence
<220> FEATURE:
<221> NAME/KEY: MISC_FEATURE
<222> LOCATION: (106)..(119)
<223> OTHER INFORMATION: SEQ ID NO: 2 sequence

<400> SEQUENCE: 8

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
```

```
                35                  40                  45
Met Gly Tyr Val Asp Asp Thr Gln Phe Val Arg Phe Asp Ser Asp Ser
 50                  55                  60
Ala Cys Pro Arg Met Glu Pro Arg Ala Pro Trp Val Glu Gln Glu Gly
 65                  70                  75                  80
Pro Glu Tyr Trp Glu Glu Thr Arg Asn Thr Lys Ala His Ala Gln
                 85                  90                  95
Thr Asp Arg Met Asn Leu Gln Thr Leu Arg Gly Tyr Tyr Asn Gln Ser
                100                 105                 110
Gly Ala Ser Ser His Thr Leu Gln Trp Met Ile Gly Cys Asp Leu Gly
                115                 120                 125
Ser Asp Gly Arg Leu Leu Arg Gly Tyr Glu Gln Tyr Ala Tyr Asp Gly
                130                 135                 140
Lys Asp Tyr Leu Ala Leu Asn Glu Asp Leu Arg Ser Trp Thr Ala Ala
145                 150                 155                 160
Asp Thr Ala Ala Gln Ile Ser Lys Arg Lys Cys Glu Ala Ala Asn Val
                165                 170                 175
Ala Glu Gln Arg Arg Ala Tyr Leu Glu Gly Thr Cys Val Glu Trp Leu
                180                 185                 190
His Arg Tyr Leu Glu Asn Gly Lys Glu Met Leu Gln Arg Ala Gly Ile
                195                 200                 205
Val Ala Gly Leu Val Val Leu Ala Ala Val Thr Gly Ala Ala Val
                210                 215                 220
Ala Ala Val Leu Trp Arg Lys Lys Ser Ser Asp
225                 230                 235

<210> SEQ ID NO 9
<211> LENGTH: 35
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (23)..(35)
<223> OTHER INFORMATION: SEQ IF NO: 1 sequence

<400> SEQUENCE: 9

Asp Ser Asp Ser Ala Cys Pro Arg Met Glu Pro Arg Ala Pro Trp Val
 1               5                  10                  15
Glu Gln Glu Gly Pro Glu Tyr Trp Glu Glu Thr Arg Asn Thr Lys
                20                  25                  30
Ala His Ala
         35

<210> SEQ ID NO 10
<211> LENGTH: 55
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (1)..(14)
<223> OTHER INFORMATION: SEQ IF NO: 2 sequence

<400> SEQUENCE: 10

Arg Gly Tyr Tyr Asn Gln Ser Glu Ala Ser Ser His Thr Leu Gln Trp
 1               5                  10                  15
Met Ile Gly Cys Asp Leu Gly Ser Asp Gly Arg Leu Leu Arg Gly Tyr
```

```
                         20                  25                  30

Glu Gln Tyr Ala Tyr Asp Gly Lys Asp Tyr Leu Ala Leu Asn Glu Asp
        35                  40                  45

Leu Arg Ser Trp Thr Ala Ala
    50                  55

<210> SEQ ID NO 11
<211> LENGTH: 60
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (48)..(60)
<223> OTHER INFORMATION: SEQ ID NO: 3 sequence

<400> SEQUENCE: 11

Asp Thr Ala Ala Gln Ile Ser Lys Arg Lys Cys Glu Ala Ala Asn Val
1               5                   10                  15

Ala Glu Gln Arg Arg Ala Tyr Leu Glu Gly Thr Cys Val Glu Trp Leu
            20                  25                  30

His Arg Tyr Leu Glu Asn Gly Lys Glu Met Leu Gln Arg Ala Asp Pro
        35                  40                  45

Pro Lys Thr His Val Thr His His Pro Val Phe Asp
    50                  55                  60

<210> SEQ ID NO 12
<211> LENGTH: 118
<212> TYPE: PRT
<213> ORGANISM: Artificial Sequence
<220> FEATURE:
<223> OTHER INFORMATION: The genetic source is human.
<220> FEATURE:
<221> NAME/KEY: MISC_FEATURE
<222> LOCATION: (73)..(83)
<223> OTHER INFORMATION: SEQ ID NO: 4 sequence

<400> SEQUENCE: 12

Tyr Glu Ala Thr Leu Arg Cys Trp Ala Leu Gly Phe Tyr Pro Ala Glu
1               5                   10                  15

Ile Ile Leu Thr Trp Gln Arg Asp Gly Glu Asp Gln Thr Gln Asp Val
            20                  25                  30

Glu Leu Val Glu Thr Arg Pro Ala Gly Asp Gly Thr Phe Gln Lys Trp
        35                  40                  45

Ala Ala Val Val Val Pro Ser Gly Glu Glu Gln Arg Tyr Thr Cys His
    50                  55                  60

Val Gln His Glu Gly Leu Pro Glu Pro Leu Met Leu Arg Trp Lys Gln
65                  70                  75                  80

Ser Ser Leu Pro Thr Ile Pro Ile Met Gly Ile Val Ala Gly Leu Val
                85                  90                  95

Val Leu Ala Ala Val Val Thr Gly Ala Ala Val Ala Ala Val Leu Trp
            100                 105                 110

Arg Lys Lys Ser Ser Asp
        115
```

BROAD SPECTRUM VACCINE, PREPARING METHOD AND APPLICATION THEREOF

BACKGROUND

Technical Field

The invention belongs to the field of biomedical technology. A method is that to use the antigenic fragment having the amino acid sequence of HLA-G to prepare a broad spectrum vaccine. Use of the broad spectrum vaccine can prevent tumor and viral disease in human and animal body.

Description of Related Art

Malignant tumor is one of the major diseases that threaten human health and life. Its incidence is increasing year by year and shows an increasing trend at younger population. According to a report of the World Health Organization (WHO) in 1997, the number of mortality for cancer patients worldwide is at 6.6 million per year, and the number is expected to reach 15 million per year by 2020. According to the latest statistics, one in every four to five deaths in China is resulted from cancer in the last 20 years, and cancer has become the number one killer of mankind.

The tumor is raging, the people are afraid, before the treatment of the effective drug development, the prevention of cancer is a great health need. However, at present, the world has not yet provided an effective tumor prevention technology, the development of advanced methods and techniques for the prevention of tumor is an urgent task.

New viruses or unknown viruses continue to appear, causing serious disasters to humans over and over again. While no effective drug has been developed to treat viral infections, it is more important to prevent infection, especially to prevent the infection of unknown or all viruses. Although humans have developed vaccines to prevent certain viruses, it is particularly important to develop a broad spectrum vaccine to prevent unknown viruses or all viruses. If a vaccine can be developed to prevent an unknown virus or all viruses, it will be able to resist an unknown virus or all viruses that attack humans. Humans are looking forward to the early release of vaccines against unknown or all viruses.

HLA-G is a non-classical HLA I class molecule. HLA-G was cloned and confirmed by Geraghty et al in 1987. HLA-G molecule has a biological function which can directly inhibit more kinds of immune active cells. HLA-G is an important immune tolerance molecule, in maternal-fetal immunity, tumor immunity, transplantation immunity, autoimmunity, and infection immunity plays an important role. Studies have shown that in tumor immunity, HLA-G inhibits NK cells, T cells and dendritic cells, thus the immune system in an inhibiting status in the body. Due to HLA-G causes immune inhibition in the human body, tumor cell can escape the immune surveillance, tumor cell obtains free growth opportunity.

The result of tumor immunohistochemical test showed that in laryngeal cancer, esophageal cancer, gastric cancer, colon cancer, rectal cancer, lung cancer, breast cancer, ovarian cancer, ovarian cancer and other malignant tumor tissues can express HLA-G. In addition, HLA-G is positive result in blood samples of HBsAg, HCAg, HIV, SARS, ebola and zika. It is showed that HLA-G expression in the tissue of tumor and viral disease patient is universal. HLA-G expected to become the common target of all tumor and viruses and HLA-G can be as an immunogen plays a role in the prevention of tumor and viral diseases. But if prepare the broad spectrum vaccine by using HLA-G molecule, the preparation needs gene hybrid, expression and purification of the upstream work. Because the big volume and high cost of upstream work, it is not conducive for the popularization, production and application of the vaccine.

The determinants of immunogen determine the specificity of antigens in immune response. There are many or more determinants in each immune molecule.

These determinants in HLA-G molecules derived from tumor or virus are expected to be used in the form of peptides as immunogenic peptides used in the active pharmaceutical ingredients of peptide vaccines. However, due to the cell of immune response to determinant in different parts of has different degree of affinity, and immunogenicity of peptide fragments may also loss in the process of forming the vaccine with the complexity of structure. The antigenic determinants in HLA-G molecules know today does not provide accurate and effective application information for preparation of broad spectrum vaccine.

SUMMARY

The present invention provides an antigen fragment, including at least one of the following amino acid sequences:

```
(1)
                                            (SEQ ID NO: 1)
YW EEE TRN TKA HA;

(2)
                                            (SEQ ID NO: 2)
RGY YNQ SEA SSH TL;

(3)
                                            (SEQ ID NO: 3)
PPK THV THH PVFD;

(4)
                                            (SEQ ID NO: 4)
PLM LRW KQS SL.
```

Among them, the described antigen fragments are identical with the sequence of any polypeptide fragment containing at least one kind of polypeptide fragment in SEQ ID NO: 1-4 in amino acid sequence of HLA-G, or the sequence of a homology, analogy, or derivatives of this polypeptide fragment. This sequence of the antigen fragment can be synthetic; Can also be preferred to HLA-G amino acid sequence acquired through a variety of ways to shorten the shear, the amino acid sequence of HLA-G can be through artificial separation of natural sequence, or through genetic recombination and the expression of synthetic methods such as secure.

Further, the HLA-G amino acid sequence includes the amino acid sequence of each isomer of the HLA-G molecule and the conservative variant, bioactive fragment or derivative of the amino acid sequence of each isomer of the HLA-G molecule. At present, the known HLA-G natural molecules has seven kinds of isomers, the 7 kinds of isomers have four different amino acid sequence (SEQ ID NO: 5-8), the four different amino acid sequence (SEQ ID NO: 5-8) can be as one kind of a preferred choice in described HLA-G amino acid sequence.

Further, described the HLA-G amino acid sequence with one of the amino acid sequence in SEQ ID NO: 5-8 have at least 15% homology, preferred to have at least 35% homology, again preferred to have at least 60%, 70%, 80% or 90% homology, preferred to have at least 95%, 96%, 97%, 98% and 99% homology.

Further, described antigenic fragment is one of the sequence in SEQ ID NO: 1-4 preferably.

Further, described antigenic fragment is one of the sequence in SEQ ID NO: 9-12.

The invention also provides an application of a broad spectrum vaccine for prevention of tumor and viral diseases prepared by the antigenic fragment.

Among them, the described tumor and virus include all the tumors and viruses which can express HLA-G, including unknown tumors and viruses. These tumors include: (1) squamous cell carcinoma of the epithelial tissue, basal cell carcinoma, adenocarcinoma, papillary adenocarcinoma, cystic adenocarcinoma, malignant pleomorphic adenoma, and transitional epithelial carcinoma; (2) is derived from mesenchymal tissue fibrosarcoma, liposarcoma, malignant fibrous tissue cell carcinoma, leiomyosarcoma and rhabdomyosarcoma, angiosarcoma, lymphatic sarcoma, osteosarcoma, chondrosarcoma, synovial sarcoma, and malignant mesothelioma, etc.; (3) lymphoma from lymphopoietic tissue and leukemia; (4) neurofibrosarcoma, malignant schwannoma, malignant glioblastoma, medulloblastoma, malignant meningioma, neuroblastoma, etc.; (5) esophageal squamous cell tumor of the digestive tract, esophageal adenocarcinoma, gastric cancer adenoma, gastric squamous cell carcinoma, hepatic cell tumor, rectal cancer, colon cancer and pancreatic cancer; (6) non-small cell lung cancer from respiratory tract; (7) is derived from the other groups of melanoma, chorionic carcinoma, ovarian cancer cell tumor, laryngeal cancer, breast cancer, seminoma, prostate cancer, cervical cancer, dysgerminoma, embryonal carcinoma and malignant teratoma, etc. These viruses include: (1) pox virus division in double-stranded DNA virus, iridescent virus, virus, herpes virus, adenovirus, HPV, polyoma virus families, more DNA virus, vesicles, African swine fever virus, etc.; (2) single stranded DNA viruses in the combined virus family, cyclones, parvovirus, etc.; (3) DNA and RNA retroviruses of the liver DNA virus family, retroviruses, pseudoviridae, transposidae, and so on; (4) double-stranded RNA viruses in the virus, double RNA virus family, bicomponent double-stranded RNA globular fungal virus, detoxividae, etc.; (5) exposed RNA viruses in exposed RNA viruses; (6) the paramyxoviruses in the negative single-stranded RNA viruses, the elastoviruses, the filovirus family, the bornavirus family, the orthonaviridae, the bunya virus, Salad virus division, etc.; (7) the light bacteriophage, arteritis virus, coronavirus, and small RNA viruses in the single-stranded RNA virus.

Preferably, these include laryngeal cancer, esophageal cancer, stomach cancer, liver cancer, pancreatic cancer, colon cancer, prostate cancer, lung cancer, breast cancer, ovarian cancer and cervical cancer. These viruses include: HBsAg, HCAg, HIV, SARS, ebola, zika, dengue virus, and avian influenza virus.

Further, the vaccine works by producing HLA-G antibodies which can bind to HLA-G in the organism through the antigenic fragment.

The present invention also provides a method for preparing a broad spectrum vaccine preventing tumor and viral diseases, including a step of using the above-mentioned antigenic fragment as immunogen.

Further, the method also involves combining the antigen fragment with the carrier protein into a complex and then purifying the complex.

Further, the complexes producing by described antigen fragments to bind with carrier protein can be obtained by using combination of coupling reagent, such as using carbodiimide, glutaraldehyde, and two isocyanate compounds, etc., can also be gained by building fusion gene expression by organisms.

Among them, the described carrier protein was preferably a hemocyanin, and the described coupling reagent was preferably a glutaraldehyde.

The antigenic fragment provided by the invention (the amino acid sequence SEQ ID NO: 1-4 and other antigenic fragments containing at least one of SEQ ID NO: 1-4) has a high degree of structural conservative and high immune activity, and can produce HLA-G antibody (HLA-G specific antibody) by through the biological immune reaction. The HLA antibody by combined with HLA-G can interdict the immune inhibition of HLA-G in the human body, cut the tumor and viral immune escape, make tumor cells and viruses easily removed by the body's immune system. The antigenic fragments provided in the present invention contain only as low as 10 amino acid residues, which greatly reduce the synthetic cost and the upstream work of vaccine preparation under the premise of maintaining its immune activity. And due to the highly conservative structure of the structure, it has the same effect as, even better than the general immune system. From the experiment data, choose the invention amino acid sequence one of the SEQ ID NO: 1-4 as a raw and processed materials to prepare vaccine, after immune animals the antibody drop degree can reach more than 1:100000 (ELISA).

The following terms are used in the specification and claims of the invention, unless otherwise stated, and the following meanings are considered to be within the knowledge of the technical personnel of the field:

"HLA-G amino acid sequence" should be interpreted in a broad sense, to include not only the HLA-G natural molecules of each isomer amino acid sequence (such as SEQ ID NO: 5-8), and also to include the conservatism variants, bioactive fragments or derivatives of the amino acid sequence of each isomer in HLA-G molecules. The conservative variant, the bioactive fragment and the derivative of the amino acid sequence in the HLA-G molecule, contain at least one of the sequence in SEQ ID NO: 1-4; These generalized HLA-G amino acid sequences themselves or any amino acid sequence of fragment contain at least one of sequence in SEQ ID NO: 1-4, these fragments can be the source of the present invention. Or, these generalized HLA-G amino acid sequences themselves or any amino acid sequence of fragment contains at least one of sequence in SEQ ID NO: 1-4 have the same amino acid sequence as the present invention.

The "amino acid sequence" only deals with the first order structure of amino acid residues (protein level 1), and does not extend to the secondary and tertiary structures that contain the sequence of amino acid sequences.

"Peptide" refers to peptides with an amino acid sequence, including oligopeptide, peptide, narrow peptide (more than 20 amino acid residues of the peptide) or a protein sequence and its segment or part, glycosylation or non glycosylation, one or more of the amino acid residues in amino acid sequence can be modified or not been modified. When its amino acid sequence of the existence of a natural amino acid sequence of the protein molecules, the "peptide" or "protein" does not mean that the amino acid sequence limit is related to the naturally occurring protein molecules complete or completely consistent natural amino acid or its sequence.

"Homology" includes completely homologous and parts, in the present invention has a relatively wide range of meanings, in describing the antigen fragments, peptides or amino acid sequence, which has the same or similar structure or function, or similar amino acid sequence, including sequence variants, analogues and derivatives; When the percentage is involved, the sequence of amino acid residues in the sequence has a certain percentage of homogeneity.

"Analogue" refers to the polypeptide which maintains basically the activity of the antigens of the present invention, as long as the analogue can combine with antibody of HLA-G which is produced by one of the sequence in SEQ ID NO: 1-4. The peptide "analogue" of the present invention can include: (I) consecutive or interval insertions and deletions, replace of one or more of the amino acid residues in a sequence, and the insertions and deletions, replace of referred to one or more of the amino acid residues at the same time or does not occur in the same sequence; (II) one or more amino acid residues group is replaced or absented by other group in the sequence; (III) one or more amino acid residues were modified in the sequence.

"Derivative" refers to primary polypeptides, proteins or sequence of amino acids are derived from the related polypeptides, proteins or sequence of amino acids when describing the sequence of peptides, proteins, or amino acids. The polypeptide, antigenic fragment, or amino acid sequence of the present invention contain the one out of the sequence in SEQ ID NO: 1-4 and use this sequence can produce HLA-G antibody which can bind to HLA-G. The non-deterministic examples of the "derivatives" of the invention may include: (IV) the fusion of mature peptides with another compound, or (V) fusion or insertion of additional amino acid sequence in the amino acid sequence (linker, protein purification identification sequence, enzyme cutting site, etc.) in amino acid sequence.

"Conservative" means that the sequence of amino acids involved has higher similarity or identity with the original sequence, and can maintain the basic structure, biological activity or function of the original sequence. The substitution of lysine and arginine, leucine and isoleucine is generally available through similar amino acid residues.

A "variant" is a sequence of amino acids which has one or more amino acid changes, and the changes can include the insertion, deletion or replacement of amino acids or nucleotides in amino acid sequences or nucleic acid sequences. Variations can be conservative change, replacement of amino acid and the original amino acid has similar structure or chemical properties, such as leucine and isoleucine between replacement, also can have a conservative change.

"Bioactive fragments" refers to the fragment can maintain basically its original activity and function in biological molecules, which may be the same with original fragment, can also be changed in the basis of the original fragment, and the position of conservative change (conservative variants) occurs general in the non function area of original fragment or non determinant area (such as liker area), but does not exclude the non original fragment occurs non conservative change. This non-original fragment can produce HLA-G antibody use by through the one out of sequence in SEQ ID NO: 1-4 as source of antigen fragment in the present invention, Or, the non-original fragment itself or any fragment of it contains at least one of the sequence in SEQ ID NO: 1-4 has the same amino acid sequence in the present invention.

"Active" when as description of antigen fragments or one of the sequence in SEQ ID NO: 1-4 in this invention, refer to antigenic fragment or one out of sequence in SEQ ID NO: 1-4 get through the immune reaction in human body or anima body can produce HLA-G antibody which can able to bind with HLA-G.

DESCRIPTION OF THE EMBODIMENTS

In addition to the definition, the meaning of technical terms used in the following implemental example was identical with the understanding of technical personnel in the field of the invention. The test reagents used in the following implemental example, such as no special instructions, are conventional biochemical reagents; the experimental methods, if no special instructions, are conventional methods.

The following described the creativity of the invention with the implemental example. In the following implemental example, the immunogen preparing the vaccine coming from market or obtained by through commercial synthesis.

Implemental Example 1

The HLA-G 1, HLA-G 5 and HLA-G 7 were used as immunogen to prepare broad spectrum vaccine. The HLA-G 1, HLA-G 5 and HLA-G 7 as three isomers of the HLA-G molecule had the same amino acid sequence (SEQ ID NO: 5), the process of preparation of vaccine was same with HLA-G 1. As an example of implemental example, the process of preparing vaccine was as follows:

33 mg HLA-G 1 was dissolved in 50 ml pH 7.4, 0.01M/L PBS solution. The concentration of HLA-G 1 was 660 mg/L. Placed the solution on an electromagnetic agitator. Placed a stirrer in the solution, and turned on the electromagnetic agitator to stir the solution of HLA-G 1. Then added 3 ml of 1 mMol/L $KAL(SO_4)_2$-$12H_2O$ solution, stirred constantly and drip added 1 ml of 1 mMoL/L NaOH solution. Continue to stir for 10 minutes, stopped stirring, 0.1 Mol/L HCL was used for adjust the pH of the solution to 7.4, after aseptic filtration, the filtrated solution placed at 4° C. for later use.

Implemental Example 2

A broad spectrum vaccine was prepared by HLA-G 2 and HLA-G 6 respectively. HLA-G 2 and HLA-G 6 were two isomers of HLA-G molecules with the same amino acid sequence (SEQ ID NO: 6). The process of preparing the vaccine was same, HLA-G 2 as an example, the process of preparing the vaccine was as follows:

24 mg HLA-G 2 was dissolved in 50 ml pH 7.4, 0.01 M/L of PBS solution. The concentration of HLA-G 2 was 480 mg/L. Placed the solution on an electromagnetic agitator, placed a stirrer in the solution, turned on the electromagnetic stirrer to stir the HLA-G 2 solution slowly. Then slowly added 2.1 ml of 1 mMol/L $KAL(SO_4)_2$-$12H_2O$ solution, stirred constantly and drip added 0.72 ml of 1 mMol/L NaOH solution, continue to stir for 10 minutes, stopped stirring, 0.1 Mol/L of HCL was used to adjust the pH of the solution to 7.4, after aseptic filtration, the filtrated solution was placed at 4° C. for later use.

Implemental Example 3

HLA-G 3 (SEQ ID NO: 7) was used as immunogen to prepare broad spectrum vaccine: 14 mg of HLA-G 3 was dissolved in 50 ml pH 7.4, 0.01 M/L PBS solution. The concentration of HLA-G 3 was 279 mg/L. Placed the solution on an electromagnetic agitator, and placed a stirrer in the solution, and turned on the electromagnetic agitator to gently stir the HLA-G 3 solution. Then slowly added 1.3 ml of 1 mMol/L KAL(SO$_4$)$_2$-12H$_2$O solution, stirred constantly and drip added 0.42 ml of 1 mMol/L NaOH solution. Continue to stir for 10 minutes, stopped stirring, 0.1 Mol/L of HCL solution was used to adjust the pH of the solution to 7.4, after aseptic filtration and filtrated solution placed at 4° C. for later use.

Implemental Example 4

HLA-G 4 (SEQ ID NO: 8) was used as immunogen to prepare broad spectrum vaccine. 23 mg HLA-G 4 was dissolved in 100 ml pH 7.4, 0.01 M/L PBS solution. The concentration of HLA-G 4 was 459 mg/L. Place the solution on an electromagnetic agitator, place a stirrer in the solution, and turn on the electromagnetic agitator to gently stir the HLA-G 4 solution. Then slowly add 2.1 ml of 1 mMol/L KAL(SO$_4$)$_2$-12H$_2$O solution, stirred constantly and drip added 0.7 ml of 1 mMOL/L NaOH solution, continue to stir for 10 minutes, stopped stirring, 0.1 Mol/L of HCL is used to adjust the pH of the solution to 7.4, after aseptic filtration place at 4° C. for later use.

Implemental Example 5 when use of two or more than two kinds of HLA-G isomer as joint immunogen, prepared broad spectrum vaccine, the operation use the basis of implemental example 1, in the 33 mg of HLA-G 1, 3 ml, of 1 mMol/L KAL(SO$_4$)$_2$-12H$_2$O solution and 1 ml of 1 mMol/L NaOH solution, the 33 mg, 3 ml and 1 ml were multiplied by n, n represents the number of kind of HLA-G isomers. For example, two kinds of isomers as the combined immunogen, n=2, three kinds of isomers as the combined immunogen, n=3. And so on.

Implemental Example 6

The polypeptide (small peptides) of SEQ ID NO: 1 was used as immunogen to prepare broad spectrum vaccine. Dissolved 33 mg hemocyanin in 50 ml pH 7.4, 0.01 mol/L PBS solution, under electromagnetic stirring, again dissolves 3.3 mg small peptide (immunogen) in above PBS solution. Continue to stir 10 minutes, take 5% glutaraldehyde solution was diluted to 1000 times by above PBS solution. Then took the diluted glutaraldehyde solution 0.15 ml with drop wise to add the above solution under the condition of stirring, continue to stir for 30 minutes, put the solution in 4° C. refrigerator overnight.

In the next day, the solution went through the sephadex-G25 chromatography column, collected 280 nanometer absorptive peaks and removed the unbounded glutaraldehyde and immunogen peptides. Then to use an affinity chromatography column of anti-HLA-G, removed hemocyanin which did not combine the small peptide of immunogen, and to use pH 3.5, 0.05 Mol/L glycine-HCL buffer desorbs hemocyanin combined with small peptide, and immediately to use 0.05 Mol/L NaOH solution neutralized the desorbed solution. To concentrates the desorbed solution appropriately. Then to use the method of implemental example 1 obtains a broad spectrum of small peptide vaccine.

Implemental Example 7

The polypeptide (small peptides) of SEQ ID NO: 2 was used as immunogen to prepare broad spectrum vaccine. Dissolved 33 mg hemocyanin in 50 ml pH 7.4, 0.01 mol/L PBS solution, under electromagnetic stirring, again dissolved 3.3 mg small peptide (immunogen), continue to stir 10 minutes, took 5% glutaraldehyde solution was diluted to 1000 times by abortive PBS solution. Then took the diluted glutaraldehyde solution 0.15 ml drop wise to added the above solution under the condition of stirring, continue to stir for 30 minutes. The above solution was put in 4° C. refrigerator overnight.

In the next day, the solution went through the sephadex-G25 chromatography column collected 280 nanometer absorptive peaks and removed the unbounded glutaraldehyde and small immunogen peptides. Then to use an affinity chromatography column of anti-HLA-G, removed the hemocyanin which did not combine the small peptide of immunogen. To use pH 3.5, 0.05 Mol/L of glycine-HCL buffer desorbed hemocyanin combined with small peptide of immunogen, and immediately to use 0.05 Mol/L NaOH solution neutralizes the desorbed solution. To concentrates the desorbed solution appropriately. Then to use of the method of implemental example 1 obtained a broad spectrum of small peptide vaccine.

Implemental Example 8

The polypeptide (small peptide) of The SEQ ID NO: 3 was used as immunogen to prepare broad spectrum vaccine. Since SEQ ID NO: 3 with SEQ ID NO: 1 had same number of amino acids, and all of them had 13 amino acids, and the molecular weight of the two was similar, so the specific operation was similar to the implemental example 6.

Implemental Example 9

The polypeptide (small peptide) of SEQ ID NO: 4 was used as immunogen to prepare broad spectrum vaccine. Dissolves the 33 mg hemocyanin in 50 ml pH 7.4, 0.01 Mol/L PBS solution, under electromagnetic stirring condition, again adds 3.3 mg immunogen small peptide, continue to stir 10 minutes, took 5% glutaraldehyde solution was diluted 1000 times by use of the PBS solution. Then took 0.15 ml of the diluted glutaraldehyde solution under the stirring condition drop wise added to the above solution, continue stirs for 30 minutes, put the solution in 4° C. refrigerator overnight.

In the next day, the solution went through the sephadex-G25 chromatography column, collected 280 nanometer absorptive peak solution and removes the unbound glutaraldehyde and immunogen peptides. Then to use an affinity chromatography column of anti-HLA-G to remove the hemocyanin which did not combine the immunogen small peptide, to use pH 3.5, 0.05 Mol/L of glycine-HCL buffer desorbs the complex compound which was hemocyanin combined with the immunogen small peptide, and immediately use of 0.05 Mol/L NaOH solution to neutralize the desorbed solution. After appropriately concentrated the desorbed solution, and again treated by use of the method of implemental example 1, obtained a broad spectrum vaccine prepared by use of immunogen small peptide.

Implemental Example 10

The SEQ ID NO: 9 peptides were used as immunogen to prepare broad spectrum vaccine. 3.3 mg immunogen polypeptide was dissolved in 50 ml pH 7.4, 0.01 M/L PBS solution. The concentration of immunogen polypeptide was 66 mg/L. Placed the solution on an electromagnetic agitator, to place a stirrer in the solution, turned on the electromagnetic stirrer, and gently stir the solution of the immunogen peptides. Then slowly added 0.3 ml, 1 mMol/L KAL(SO$_4$)$_2$-12H$_2$O solution, stirred constantly, and drip added 0.1 ml 1 mMol/L of NaOH solution, continue to stir for 10 minutes, stopped stirring, 0.1 Mol/L of HCL was used to adjust the pH of the solution to 7.4, after aseptic filtration, the filtrated solution is placed at 4° C. for storage.

Implemental Example 11

The SEQ ID NO: 10 peptide was used as immunogen to prepare broad spectrum vaccine. 5.3 mg immunogen polypeptide was dissolved in 50 ml pH 7.4, 0.01M/L Of PBS solution. The concentration of immunogen polypeptide was 66 mg/L. Placed the solution on an electromagnetic agitator and to place a stirrer in the solution, turned on the electromagnetic stirrer, and gently to stir the solution of the immunogen peptide. Then slowly to add 0.48 ml, 1 mMol/L of KAL(SO$_4$)$_2$-12H$_2$O solution, stirred constantly, and drip added 0.16 ml, 1 mMol/L of NaOH solution, continue to stir for 10 minutes, stopped stirring, 0.1 Mol/L of HCL was used to adjust the pH of the solution to 7.4, after aseptic filtration to place at 4° C. store.

Implemental Example 12

The SEQ ID NO: 11 peptides were used as immunogen to prepare broad spectrum vaccine. 5.9 mg immunogen polypeptide was dissolved in 50 ml pH 7.4, 0.01M/L of PBS solution. The concentration of immunogen polypeptide was 119 mg/L. Place the solution on an electromagnetic agitator, to place a stirrer in the solution, turn on the electromagnetic stirrer, and gently to stir the solution of the immunogen peptides. Then slowly to add 0.54 ml, 1 mMol/L of KAL(SO$_4$)$_2$-12H$_2$O solution, stirred constantly, and drip added 0.18 ml 1 mMol/L of NaOH solution, continue to stir for 10 minutes, stopped stirring, 0.1 Mol/L of HCL was used to adjust the pH of the solution to 7.4, after aseptic filtration, the filtered solution is placed at 4° C. for storage.

Implemental Example 13

The SEQ ID NO: 12 peptides were used as immunogen to prepare broad spectrum vaccine. 11.6 mg immunogen polypeptide was dissolved in 50 ml pH 7.4, 0.01M/L of PBS solution. The concentration of immunogen polypeptide was 231 mg/L. Placed the solution on an electromagnetic agitator, to place a stirrer in the solution, turned on the electromagnetic stirrer, and gently to stir the solution of the immunogen peptides. Then slowly to add 1.1 ml, 1 mMol/L of KAL(SO$_4$)$_2$-12H$_2$O solution, stirred constantly, and drip added 0.35 ml, 1 mMol/L of NaOH solution, continue to stir for 10 minutes, stopped stifling, 0.1 Mol/L of HCL was used to adjust the pH of the solution to 7.4, after aseptic filtration, the filtered solution is placed at 4° C. for storage.

Implemental Example 14

The experiment preventing tumor in sensitized rabbits:
The experimental group took 9 healthy adult rabbits, divided into three groups of A, B, and C, 3 rabbits in each group, the control group took the normal adult 9 rabbits, also divided into three groups of A, B, and C, 3 rabbits in each group. The experimental group was immunized by broad spectrum vaccine. The experimental A group was immunized by the vaccine obtained from the example 1, the experimental B group was immunized by the vaccine obtained from the example 6, the experimental C group was immunized by the vaccine obtained from experiment 10.

The dose of immune was 20 micrograms/kg, once of every 10 days subcutaneous injection for 3 times. When the titer of antibody reached high than 1:10 thousand (ELISA), the immunization was stop. The control group was immunized by use of pH 7.4, 0.01 mol/L PBS and 1 ml using for each times, total injection need 3 times.

The experiment of inoculation of tumor cell: the rabbits of experiment group and control group were injected was same number of ovarian tumor cell lines A2780, 0.5 ml of 2000 /ml, 3 dot of subcutaneous injection. After 1-2 months of observation, tumor cell was not found in the experimental group, the protection rate was 100%, while the control group all of the rabbits had tumors. Experimental results show that HLA-G broad spectrum vaccine was effective in prevention of cancer.

Implemental Example 15

To use the identical method with implemental example 14 did preventive experiment for prevention of other tumors. The experimental process and the dosage of reagent could be conventional adjusted according to the needs of different tumor models and it was easily for the technical person in this field. The various kinds of vaccines obtained in the implemental example 1 to 13 in the invention took part in the experiment preventing tumor model at not less than five kinds of animal tumor. After immunization used the vaccines in this invent, the result that the experiment group did not found tumor growth, and the control group all of the rabbits had tumor growth.

These tumors include: (1) squamous cell carcinoma of the epithelial tissue, basal cell carcinoma, adenocarcinoma, papillary adenocarcinoma, cystic adenocarcinoma, malignant pleomorphic adenoma, and transitional epithelial carcinoma; (2) is derived from mesenchymal tissue fibrosarcoma, liposarcoma, malignant fibrous tissue cell carcinoma, leiomyosarcoma and rhabdomyosarcoma, angiosarcoma, lymphatic sarcoma, osteosarcoma, chondrosarcoma, synovial sarcoma, and malignant mesothelioma, etc.; (3) lymphoma and leukemia from lymphopoietic tissue; (4) neurofibrosarcoma, malignant schwannoma, malignant glioblastoma, medulloblastoma, malignant meningioma, neuroblastoma, etc.; (5) esophageal squamous cell tumor of the digestive tract, esophageal adenocarcinoma, gastric cancer adenoma, gastric squamous cell carcinoma, hepatic cell tumor, rectal cancer, colon cancer and pancreatic cancer; (6) non-small cell lung cancer from respiratory tract; (7) is derived from the other groups of melanoma, chorionic carcinoma, ovarian cancer cell tumor, laryngeal cancer, breast cancer, seminoma, prostate cancer, cervical cancer, dysgerminoma, embryonal carcinoma and malignant teratoma, etc.

Implemental Example 16: To Prevent Virus Attack in Sensitized Rabbits

The experimental group collected 9 healthy adult rabbits, divided into three groups of A, B and C, 3 rabbits in ach group, and the control group took 9 normal adult rabbits. Experimental group was immunized by the broad spectrum vaccine, the rabbits in group A immunized by the vaccine obtained in implementation example 2, the rabbits in group B immunized by the vaccine obtained in the implementation 7, and group C immunized by use of the vaccine obtained in implementation 11. when immune titer of the antibody reached more than 1:50000 (ELISA), to stop the immunization. The rabbits of control group were immunized by use of pH 7.4, 0.01 mol/L PBS.

The experimental group and the control group inoculated the same dose of avian influenza virus (0.05-1.0 microgram/kg/time). The infection was carried out by drop in eye or nose, once a day, with a total infection of 2 times, and observed for 5-20 days. Statistics of the number of rabbits in the experimental group and the control group was attacked. Experimental results showed that none of the nine rabbits were attacked in the experimental group, and had a 100% protection rate. The all of nine rabbits in the control group were all ill. The experimental results confirmed that this vaccine has the effective function for preventing avian influenza virus.

Implemental Example 17

The same method with experiment 16 was used for the experiment of prevention of other viruses. The experimental process and dosage of reagent could be conventional adjusted according to the needs of different virus infective models, it was easy for the technical person in this field.

All kinds of vaccines obtained in the implemental example of 1-13 of this invent took part in preventive experiments of virus infective model at no less than 5 kinds of virus infective model. The experimental result shown that after immunization used the vaccines obtained from this invention, the experimental rabbits were found no infected with the virus, whereas the control rabbits were infected with viral diseases.

These viruses include: (1) pox virus division in double-stranded DNA virus, iridescent virus, virus, herpes virus, adenovirus, HPV, polyoma virus families, more DNA virus, vesicles, African swine fever virus, etc.; (2) single stranded DNA viruses in the combined virus family, cyclones, parvovirus, etc.; (3) DNA and RNA retroviruses of the liver DNA virus family, retroviruses, pseudoviridae, transposidae, and so on; (4) double-stranded RNA viruses in the virus, double RNA virus family, bicomponent double-stranded RNA globular fungal virus, detoxividae, etc.; (5) exposed RNA viruses in exposed RNA viruses; (6) the paramyxoviruses in the negative single-stranded RNA viruses, the elastoviruses, the filovirus family, the bornavirus family, the orthonaviridae, the bunya virus family, the salavirus family, and so on; (7) the light bacteriophage, arteritis virus, coronavirus, and small RNA viruses in the single-stranded RNA virus.

Described above is only a preferred example of this invention, not to limit creation of the invention. All of within the spirits and principles of the invention, by any modification, equivalent replacement, improvement, etc., shall be contained within the protection scope of the invention.

What is claimed is:

1. A broad spectrum vaccine for preventing various kinds of tumors and various kinds of viral diseases, wherein the broad spectrum vaccine is prepared with an antigenic fragment; the antigenic fragment consists of at least one of amino acid sequences in SEQ ID NO: 1-4; the tumors and the viral diseases comprise the tumors and virus that express HLA-G;

wherein, SEQ ID NO:1 is YW EEE TRN TKA HA;
SEQ ID NO:2 is RGY YNQ SEA SSH TL;
SEQ ID NO:3 is PPK THV THH PVFD;
SEQ ID NO:4 is PLM LRW KQS SL;
the vaccine works by producing HLA-G antibodies which bind to HLA-G;
where in the broad spectrum vaccine is prepared by combining the antigen fragment with a carrier protein into a complex and then purifying the complex.

2. A method of preparing the broad spectrum vaccine according to the claim 1 to prevent various kinds of tumors and various kinds of viral diseases, wherein the broad spectrum vaccine is prepared with an antigenic fragment; the antigenic fragment consists of at least one of amino acid sequences in SEQ ID NO: 1-4;
wherein, SEQ ID NO:1 is YW EEE TRN TKA HA;
SEQ ID NO:2 is RGY YNQ SEA SSH TL;
SEQ ID NO:3 is PPK THV THH PVFD;
SEQ ID NO:4 is PLM LRW KQS SL;
wherein the broad spectrum vaccine is prepared by combining the antigen fragment with a carrier protein into a complex and then purifying the complex.

3. The method of preparing of the broad spectrum vaccine according to the claim 2, wherein the tumors and the viral diseases express HLA-G, the tumors comprise: (1) squamous call carcinoma of the epithelial tissue, basal cell carcinoma, adenocarcinoma, papillary adnocarcinoma, cystic adnocarcinoma, malignant pleomorphic adnoma, and transitional epithelial carcinoma which root in the epithelial tissue; (2) fibrosarcoma, malignant fibrous tissue cell carcinoma, liposarcoma, leionyosacoma and rhabdomyosarcoma, angiosarcoma, lymphaticsarcoma, osteosarcoma, chondrosarcoma, synovial sarcoma, and malignant mesothelioma; (3) lymphoma and leukemia from lymphopoietic tissue;(4) neurofibrosarcoma, malignant schwannoma, malignant glioblastoma, medulloblastoma, malignant meningioma, neuroblastoma; (5) esophageal squamous cell tumor of the digestive tract, esophageal adenocarcinoma, gastric cancer adenoma, gastric squamous cell carcinoma, hepatic cell tumor, rectal cancer, colon cancer and pancreatic cancer; (6) non-small cell lung cancer from respiratory tract; (7) and melanoma, chorionic carcinoma, ovarian cancer cell tumor, laryngeal cancer, breast cancer, seminoma, prostate cancer, cervical cancer, dysgerminoma, embryonal carcinoma and malignant teratoma, the viruses of the viral diseases comprise: (1) pox virus division in double-stranded DNA virus, iridescent virus, virus, herpes virus, adenovirus, HPV, polyoma virus families, DNA virus, African swine fever virus; (2) single stranded DNA viruses in the combined virus family, parvovirus; (3), retroviruses, pseudoviridae; (4) double-stranded RNA viruses in the, double-stranded RNA virus family, double-stranded RNA globular fungal virus; (5) the paramyxoviruses in the negative single-stranded RNA viruses, the filovirus family, the bornavirus family, the orthonaviridae, the bunya virus family; (6) arteritis virus, coronavirus, and small RNA viruses in the single-stranded RNA virus.

4. The method of preparing the broad spectrum vaccine according to the claim 2, wherein the complex is obtained by using carbodiimide, glutaraldehyde, and diisocyanic acid compound or obtained by building fusion gene expression by organisms.

5. The method of preparing the broad spectrum vaccine according to the claim 4, wherein the carrier protein is a hemocyanin, and coupling reagent is aglutaraldehyde.

6. The method of preparing the broad spectrum vaccine according to the claim 2, wherein the tumors comprise: laryngeal cancer, esophageal cancer, stomach cancer, liver cancer, pancreatic cancer, colon cancer, prostate cancer, lung cancer, breast cancer, ovarian cancer and cervical cancer; the viruses of the viral diseases comprise:

HBsAg, HCAg, HIV, SARS, ebola, zika, dengue virus, and avian influenza virus.

* * * * *